United States Patent [19]
Gaffney et al.

[11] Patent Number: 5,891,688
[45] Date of Patent: Apr. 6, 1999

[54] DNA ENCODING LEMA-INDEPENDENT GACA AND ITS USE IN ACTIVATING GENE EXPRESSION

[75] Inventors: Thomas D. Gaffney, Chapel Hill; Stephen T. Lam, Raleigh, both of N.C.

[73] Assignee: Novartis Finance Corporation, New York, N.Y.

[21] Appl. No.: 9,218

[22] Filed: Jan. 20, 1998

Related U.S. Application Data

[63] Continuation-in-part of Ser. No. 761,258, Dec. 6, 1996, Pat. No. 5,756,087, and a continuation-in-part of Ser. No. 977,306, Nov. 25, 1997.

[51] Int. Cl.⁶ .............................. C07K 14/21; C12N 1/21; C12N 15/31; C12N 15/63
[52] U.S. Cl. ..................................... 435/172.3; 435/252.3; 435/252.34; 435/320.1; 530/350; 536/23.7
[58] Field of Search ........................ 536/23.7; 435/320.1, 435/172.3, 252.3, 252.34; 530/350

[56] References Cited

U.S. PATENT DOCUMENTS

| | | | |
|---|---|---|---|
| 5,348,742 | 9/1994 | Howell et al. | 424/93.47 |
| 5,496,547 | 3/1996 | Lam et al. | 424/93.47 |
| 5,670,350 | 9/1997 | Gaffney et al. | 435/172.3 |
| 5,710,031 | 1/1998 | Gaffney et al. | 435/172.3 |

FOREIGN PATENT DOCUMENTS

| | | |
|---|---|---|
| 472494 | 2/1992 | European Pat. Off. |
| WO94/01561 | 1/1994 | WIPO . |
| WO95/33818 | 12/1995 | WIPO . |

OTHER PUBLICATIONS

Corbell et al., "A Global Regulator of Secondary Metabolite Production in *Pseudomonas fluorescens* PF–5", *Journal of Bacteriology*, 177(21): 6230–6236 (1995).

Gaffney et al., "Global Regulation of Expression of Antifungal Factors by a *Pseudomonas fluorescens* Biological Control Strain", *Molecular Plant–Microbe Interactions*, 7(4): 455–463 (1994).

Hrabak et al., "The lemA Gene Required for Pathogenicity of *Pseudomonas syringae* pv. Syringae on Bean Is a Member of a Family of Two–Component Regulators", *J. of Bacteriology*, 174(9): 3011–3020 (1992).

Laville et al., "Global control in *Pseudomnas fluroescens* mediating antibiotic synthesis and suppression of black root rot of tabacco", *Proc. Natl. Acad. Sci.*, 39:1562–1566 (1992).

Liao et al., "Molecular Characterization of Two Gene Loci Required for Production of the Key Pathogenicity Factor Pectate Lyase in *Pseudomonas viridiflava*", *Molecular Plant–Microbe Interactions*, 7(3): 391–400 (1994).

*Primary Examiner*—Johnny F. Railey, II
*Attorney, Agent, or Firm*—J. Timothy Meigs

[57] ABSTRACT

The present invention exploits the discovery that certain single base changes in the gacA gene coding sequence, which result in certain single amino acid changes in the encoded GacA protein, render it LemA-independent. The present invention therefore provides DNA that encodes mutant GacA proteins that do not require phosphorylation by LemA in order to be active as transcriptional activators.

28 Claims, No Drawings

DNA ENCODING LEMA-INDEPENDENT GACA AND ITS USE IN ACTIVATING GENE EXPRESSION

The present application is a continuation-in-part of U.S. application Ser. No. 08/761,258, filed Dec. 6, 1996, mow U.S. Pat. No. 5,756,087, incorporated herein by reference. The present application is also a continuation-in-part of U.S. application Ser. No. 08/977,306, filed Nov. 25, 1997, incorporated herein by reference. The present application also claims the benefit of U.S. provisional application no. 60/058,304, filed Sep. 9, 1997, incorporated herein by reference.

FIELD OF THE INVENTION

The present invention relates to the genetic elements that contribute to the activation of genes in bacterial strains. More specifically, the invention relates to DNA that encodes a mutant LemA-independent GacA global transcriptional activating element and its use in activating gene expression in transgenic bacterial strains.

BACKGROUND OF THE INVENTION

Many Pseudomonas strains produce antifungal metabolites that have been implicated in the control of fungal pathogens in the rhizosphere. For example, Howell et al. (Phytopathology 69: 480–482 (1979)) disclose a strain of *Pseudomonas fluorescens* that produces an antibiotic substance antagonistic to *Rhizoctonia solani*. In addition, other strains of *Pseudomonas fluorescens* having enhanced biocontrol activity against plant pathogenic fungi such as Rhizoctonia and Pythium have been more recently been disclosed. *Pseudomonas fluorescens* strain CGA267356 (also known as both MOCG134 and BL915) has been shown to be effective in controlling plant pathogenic fungi such as Rhizoctonia and Pythium. Strain CGA267356 is one of the subjects of U.S. Pat. No. 5,348,742, incorporated herein by reference. Two mutants of CGA267356, strains CGA321730 (a.k.a. MOCG134-8392) and CGA319115, have been constructed and shown to demonstrate even better biological control (biocontrol) of these phytopathogens. CGA321730 and CGA319115 are the subject of U.S. Pat. No. 5,496,547, incorporated herein by reference.

A particularly effective antibiotic against fungal pathogens is pyrrolnitrin, which is biosynthesized from tryptophan. Pyrrolnitrin is a phenylpyrrole derivative with strong antibiotic activity that has been shown to inhibit a broad range of fungi. Pyrrolnitrin was originally isolated from *Pseudomonas pyrrocinia*, but has since been isolated from Myxococcus species, Burkholdaria species, and several other Pseudomonas species such as *P. fluorescens*. The compound has been reported to inhibit fungal respiratory electron transport and uncouple oxidative phosphorylation. It has also been proposed that pyrrolnitrin causes generalized lipoprotein membrane damage. U.S. patent application Ser. No. 08/729,214, incorporated herein by reference, describes the cloning and characterization of the pyrrolnitrin biosynthesis genes from *P. fluorescens, P. pyrrocinia, Burkholdaria cepacia*, and *Myxococcus fulvus*.

Two genes have been isolated from strain CGA267356 that encode proteins that regulate the synthesis of several antifungal compounds produced by the strain, including pyrrolnitrin. These are the lemA gene and gacA (a.k.a. gafA) gene that encode sensor kinase and response regulator proteins, respectively, which function as a typical two-component bacterial regulatory system. In a normal regulatory system and under the proper conditions, the LemA protein phosphorylates GacA. In the phosphorylated state, GacA activates transcription of genes involved in the synthesis of antifungal compounds, i.e, the pyrrolnitrin biosynthesis genes. The lemA and gacA genes and their use to activate biocontrol activity in biocontrol strains are described in U.S. Pat. No. 5,670,350, incorporated herein by by reference. The lemA and gacA regulatory genes and the pyrrolnitrin biosynthetic genes have been utilized to genetically modify *P. fluorescens* strains to construct altered strains that demonstrate enhanced production of antifungal metabolites, i.e. pyrrolnitrin, and accordingly enhanced biocontrol activity.

SUMMARY OF THE INVENTION

The present invention exploits the discovery that certain single base changes in the gacA gene coding sequence, which result in certain single amino acid changes in the encoded GacA protein, render it LemA-independent. That is, certain single amino acid changes in the GacA protein renders it active irrespective of the kinase activity of the LemA protein. These mutant GacA proteins do not require phosphorylation by LemA in order to be active as transcriptional activators.

The native gacA nucleotide sequence from *P. fluorescens* is provided in SEQ ID NO:1, and the amino acid sequence of the native GacA regulatory protein encoded thereby is provided in SEQ ID NO:2. Applicant has discovered that changing the native guanine (G) base at position 60 to an adenine (A), and thereby changing the encoded amino acid residue 20 from the native methionine to isoleucine, renders the thus-mutated GacA protein LemA-independent. Applicant has further discovered that changing the native guanine (G) base at position 313 to an adenine (A), and thereby changing the encoded amino acid residue 105 from the native glycine to arginine, renders the thus-mutated GacA protein LemA-independent. Applicant has additionally discovered that changing the native adenine (A) base at position 395 to a guanine (G), and thereby changing the encoded amino acid residue 132 from the native glutamine to arginine, renders the thus-mutated GacA protein LemA-independent. Applicant has also discovered that changing the native guanine (G) base at position 251 to an adenine (A), and thereby changing the encoded amino acid residue 84 from the native cysteine to tyrosine, renders the thus-mutated GacA protein LemA-independent.

Thus, the present invention provides an isolated DNA molecule that encodes a LemA-independent GacA transcriptional activation element. In one preferred embodiment, the DNA molecule of the invention is isolated from a Pseudomonas species. In an especially preferred embodiment, the DNA molecule of the invention is isolated from *Pseudomonas fluorescens*.

In one embodiment, the DNA molecule that encodes a LemA-independent GacA transcriptional activation element hybridizes under the following conditions to the nucleotide sequence set forth in SEQ ID NO:1:hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6XSSC for 15 min. (X3) 3XSSC for 15 min. (X1) at 55° C.

In one aspect, the LemA-independent GacA transcriptional activation element has an isoleucine instead of a methionine residue in an amino acid position corresponding to position 20 of SEQ ID NO:2. In another aspect, the LemA-independent GacA transcriptional activation element has an arginine instead of a glycine residue in an amino acid position corresponding to position 105 of SEQ ID NO:2. In yet another aspect, the LemA-independent GacA transcriptional activation element has an arginine instead of a glutamine residue in an amino acid position corresponding to position 132 of SEQ ID NO:2. In still another aspect, the LemA-independent GacA transcriptional activation element has a tyrosine instead of a cysteine residue in an amino acid position corresponding to position 84 of SEQ ID NO:2. By "correspond to," it is meant that when the encoded amino acid sequence of an allele of gacA is aligned with the amino acid sequence (SEQ ID NO:2) encoded by the *P. fluorescens* gacA gene described herein, the amino acids in the allelic sequence that "correspond to" certain specified positions of SEQ ID NO:2 are those that align with these positions of SEQ ID NO:2, but are not necessarily in these exact positions of the allelic sequence.

In a preferred embodiment, the LemA-independent GacA transcriptional activation element comprises the amino acid sequence shown in SEQ ID NO:8; in an especially preferred embodiment, the DNA molecule of the invention comprises the nucleotide sequence shown in SEQ ID NO:7. In another embodiment, the LemA-independent GacA transcriptional activation element comprises the amino acid sequence shown in SEQ ID NO:4; according to this embodiment, the DNA molecule of the invention preferably comprises the nucleotide sequence shown in SEQ ID NO:3. In yet another embodiment, the LemA-independent GacA transcriptional activation element comprises the amino acid sequence shown in SEQ ID NO:6; according to this embodiment, the DNA molecule of the invention preferably comprises the nucleotide sequence shown in SEQ ID NO:5. In still another embodiment, the LemA-independent GacA transcriptional activation element comprises the amino acid sequence shown in SEQ ID NO:10; according to this embodiment, the DNA molecule of the invention preferably comprises the nucleotide sequence shown in SEQ ID NO:9.

The present invention also encompasses a chimeric gene comprising a promoter operatively linked to the DNA molecule of the invention, a recombinant vector comprising said chimeric gene, wherein said vector is capable of being stably transformed into a host cell, and a host cell stably transformed with said vector, wherein said host cell is capable of expressing said DNA molecule. The host cell is preferably a bacterial cell, more preferably Pseudomonas, and most preferably, *Pseudomonas fluorescens*.

In still another aspect, the present invention encompasses an isolated LemA-independent GacA transcriptional activation element. In preferred embodiments, the transcriptional activation element of the invention comprises the amino acid sequence set forth in SEQ ID NO:4, 6, 8, or 10.

The present invention further encompasses a method of activating a gene that is latent or natively expressed at low levels in a bacterial strain by introducing into said bacterial strain a DNA molecule that encodes a LemA-independent GacA transcriptional activation element. In a preferred embodiment, the bacterial strain is Pseudomonas. In an especially preferred embodiment, the bacterial strain is *Pseudomonas fluorescens*.

The present invention additionally encompasses a method of rendering a bacterial strain effective against fungal pathogens by introducing into said bacterial strain a DNA molecule that encodes a LemA-independent GacA transcriptional activation element. In a preferred embodiment, the bacterial strain is Pseudomonas. In an especially preferred embodiment, the bacterial strain is *Pseudomonas fluorescens*.

The present invention also encompasses a method for isolating a DNA molecule that encodes a LemA-independent GacA transcriptional activation element. Such a method preferably comprises the steps of (a) mutating a native gacA gene; (b) providing a lemA-minus bacterial strain, said strain comprising a reporter gene that requires active GacA for expression of said reporter gene; (c) transforming said mutated gacA gene into the strain of step (b); and (d) screening for expression of said reporter gene, whereby expression of said reporter gene indicates that said mutated gacA gene is LemA independent.

BRIEF DESCRIPTION OF THE SEQUENCES IN THE SEQUENCE LISTING

SEQ ID NO:1 is the nucleotide sequence of the native gacA regulatory gene.

SEQ ID NO:2 is the protein sequence encoded by the native gacA regulatory gene.

SEQ ID NO:3 is the nucleotide sequence of the gac*1 regulatory gene, wherein the base at position 60 has been changed from the native guanine (G) to an adenine (A) so that codon 20 encodes an isoleucine residue instead of the usual methionine.

SEQ ID NO:4 is the protein sequence encoded by the altered gac*1 regulatory gene of SEQ ID NO:3.

SEQ ID NO:5 is the nucleotide sequence of the gac*2 regulatory gene, wherein the base at position 313 has been changed from the native guanine (G) to an adenine (A) so that codon 105 encodes an arginine residue instead of the usual glycine.

SEQ ID NO:6 is the protein sequence encoded by the altered gac*2 regulatory gene of SEQ ID NO:5.

SEQ ID NO:7 is the nucleotide sequence of the gac*3 regulatory gene, wherein the base at position 395 has been changed from the native adenine (A) to a guanine (G) so that codon 132 encodes an arginine residue instead of the usual glutamine.

SEQ ID NO:8 is the protein sequence encoded by the altered gac*3 regulatory gene of SEQ ID NO:7.

SEQ ID NO:9 is the nucleotide sequence of the gac*4 regulatory gene, wherein the base at position 251 has been changed from the native guanine (G) to an adenine (A) so that codon 84 encodes a tyrosine residue instead of the usual cysteine.

SEQ ID NO:10 is the protein sequence encoded by the altered gac*4 regulatory gene of SEQ ID NO:9.

DETAILED DESCRIPTION OF THE INVENTION

The present invention provides isolated DNA molecules that encode LemA-independent GacA transcriptional activation elements. Mutant GacA proteins according to the invention each have a particular single amino acid change that renders them active irrespective of the kinase activity of the LemA protein. These mutant GacA proteins do not require phosphorylation by LemA in order to be active as transcriptional activators.

Native gacA genes (SEQ ID NO:1) can be mutated by introducing them on plasmids into the hypermutagenic *E. coli* strain XL1-Red. The plasmids are then recovered and introduced into a lemA-minus mutant of strain CGA267356 that also contains a report gene such as lacZY (U.S. Pat. No. 5,397,697) inserted into a gene whose expression is regulated by native LemA-dependent GacA. Clones containing randomly mutated gacA genes that result in expression of the lacZY genes, as indicated by the formation of blue colonies on agar containing X-Gal, contain gacA genes that do not require phosphorylation by LemA in order to be active as transcriptional activators. As shown in the Examples, infra, four such gacA genes (gac* 1, gac*2, gac*3, and gac*4) were isolated in this manner and the nucleotide sequence of each has been determined (SEQ ID NOs:3, 5, 7, and 9, respectively). In each, there is a different single base change that results in different single amino acid changes in the encoded GacA proteins (SEQ ID NOs:4, 6, 8, and 10).

The mutant gacA genes of the invention may be used to construct improved biocontrol strains of Pseudomonas that can be used to control pathogenic attack on crop plants. Such strains are able to aggressively compete in the plant rhizosphere as well as produce one or more antifungal substances such as pyrrolnitrin that are effective against a broad spectrum of plant pathogenic fungi such as Rhizoctonia and Pythium.

The biocontrol strains of the present invention are important for several reasons. First, Rhizoctonia such as *Rhizoctonia solani* are particularly pernicious plant pathogens. The affected plants include beans, wheat, tomato and potato, in addition to cotton. Second, there are few environmentally safe and effective fungicide treatments available for the protection of crops from Rhizoctonia. Therefore, the use of the disclosed biocontrol strains to control or prevent Rhizoctonia infections in crop plants provides an environmentally safe and effective method of controlling this and other plant pathogens.

A further embodiment of the invention provides a method for controlling or inhibiting the growth of a plant pathogenic fungus by applying the genetically engineered biocontrol strains of the invention to an environment in which the plant pathogenic fungus may grow. This can be to the plant/s or parts of the plant/s (before or after harvest) or to the seeds (prior to planting) of the plant/s to be protected, or alternatively to soil in which the plant/s to be protected are growing or will grow. The biocontrol strains are applied in an effective amount; that is, in an amount sufficient to control or inhibit the pathogen. The rate of application may vary according to the crop to be protected, the efficacy of the biocontrol strain, the pathogen to be controlled, and the severity of the disease pressure. Generally, the rate of application is about $1.3 \times 10^5$ cfu/cm to about $1.3 \times 10^{10}$ cfu/cm, specifically about $1.3 \times 10^6$ cfu/cm to about $1.3 \times 10^9$ cfu/cm, more specifically about $1.3 \times 10^7$ cfu/cm to about $1.3 \times 10^8$ cfu/cm.

The recombinant biocontrol strains of the present invention may be used in any manner known in the art, including coating seeds with an effective amount of the biocontrol strains, in furrow application of the biocontrol strains directly into the soil, in foliar application, and in post-harvest disease control. Such methods are well known in the art and are described, for example, in U.S. Pat. No. 5,348,742 and in the published European Application EP 0 472 494 A2, which is hereby incorporated by reference. Furthermore, the strains of this application can also be mixed in formulation with known pesticides in a manner described in WO 94/10845, which disclosure is herein incorporated by reference.

The invention is illustrated in further detail by the following detailed procedures, preparations, and examples. The examples are for illustration only, and are not to be construed as limiting the scope of the present invention.

EXAMPLES

Standard recombinant DNA and molecular cloning techniques used here are well known in the art and are described by Sambrook, et al, *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

EXAMPLE 1

Construction of Strain CGA375260 (MONO570) (gac*3)

Strain CGA375260 (a.k.a. MONO570) differs from parent strain CGA267356 (U.S. Pat. No. 5,348,742) by a single base change within the coding sequence of the native gacA gene (SEQ ID NO:1). This modification was generated by introducing the native gacA gene into the hypermutagenic *E. coli* strain XL1-Red (from Stratagene, Inc.). The plasmids were recovered and introduced into a lemA-minus mutant of strain CGA267356 that also contained lacZY reporter genes (U.S. Pat. No. 5,397,697, incorporated herein by reference) inserted into an unknown chromosomal gene whose expression is regulated by GacA (and LemA). Clones containing randomly mutated gacA genes that resulted in expression of the lacZY genes, as indicated by the formation of blue colonies on agar containing X-Gal, were further analyzed. These clones contained gacA genes that did not require phosphorylation by LemA in order to be active as a transcriptional activator. Four such gacA genes (gac*1, gac*2, gac*3, and gac*4) were isolated in this manner and the nucleotide sequence of each was determined (SEQ ID NOs: 3, 5, 7, and 9, respectively). In each, there was a different single base change that resulted in a different single amino acid change in the encoded GacA protein. Each of the four modified gacA genes were used to replace the native gacA gene in strain CGA267356 by perfect site replacement mediated through homologous recombination.

Of the four, one clone with a LemA-independent gacA gene (gac*3) has been shown to have enhanced pyrrolnitrin synthesis and biocontrol activity (Tables 1 and 2). The nucleotide sequence of the gac*3 gene of this clone, CGA375260, was determined (SEQ ID NO:7) and it was found that a single base change occurs in codon 132, which is CAG and encodes a glutamine residue in the native GacA protein. The adenine base in this codon was changed to guanine to create a codon that encodes an arginine residue (CGG) in the altered strain. Therefore, the GacA protein (SEQ ID NO:6) in this strain has an arginine at amino acid 132 instead of the usual glutamine. In all other respects, this strain is identical to the parent strain. In the normal regulatory system and under the proper conditions, the LemA protein phosphorylates GacA and in the phosphorylated state it activates transcription of genes involved in the synthesis of antifungal compounds. This single base change in the GacA protein renders it active irrespective of the kinase activity of the LemA protein.

Strain CGA375260 was deposited with the NRRL on Sep. 5, 1997, and assigned accession no. NRRL (Aicultural Research Service, Patent Culture Collection, Northern Regional Research Center, 1815 North University Street, Peoria, Ill. 61604, U.S.A) B-21816.

EXAMPLE 2
Construction of Strain NoA402208 (MONO630) (gac*3, pPrn)

Strain NOA402208 (a.k.a. MONO630) was constructed by introducing the plasmid pPrn containing the prnABCD gene cluster under the control of the tac promoter into *P. fluorescens* strain CGA375260 (Example 1) by conjugation.

Plasmid pPrn was constructed by cloning a 6.2 kb XbaI/NotI gene fragment from plasmid pCIB169 (which was derived from *P. fluorescens* strain CGA267356) into the expression vector pKK223-3, as described in Examples 7–11 of U.S. Pat. No. 5,639,949, incorporated herein by reference. Plasmid pCIB169 has been deposited with the NRRL and assigned accession number NRRL B-21256. The 6.2 kb XbaI/NotI gene fragment from plasmid pCIB169 contains the prnABCD gene cluster that encodes genes for the biosynthesis of pyrrolnitrin as described in Pat. No. 5,639,949. A 6.9 kb BglII fragment containing the prnABCD gene cluster with the tac promoter upstream of the gene cluster and the rrnB transcription terminator derived from plasmid pKK223-3 downstream of the cluster was subsequently cloned into the BglII site of plasmid pRK290 to create plasmid pPrn. The tac promoter is a small DNA fragment (less than 100 bases) derived from *E. coli*, which is known to be a regulatory element or promoter (Amann, et al, Gene 25:167–178 (1983)) that does not itself encode a protein product. The tac promoter is known to be highly expressed in a constitutive manner in Pseudomonas. Its use with the prn genes causes constitutive, high-level expression of these genes.

Strain NOA402208 produces more pyrrolnitrin (Table 1) and has greater biocontrol activity (Table 2) than parent strain CGA267356. Strain NOA402208 was deposited with the NRRL (Agricultural Research Service, Patent Culture Collection, Northern Regional Research Center, 1815 North University Street, Peoria, Ill. 61604, U.S.A) on Nov. 20, 1997, and assigned accession no. NRRL B-21891.

EXAMPLE 3
Construction of Strain NOA402212 (MONO634) (gac*3, res, pPrn)

Strain NOA402212 was constructed from *P. fluorescens* strain CGA375260 (Example 1) by deletion of a region of the chromosome that resulted in no production of the antimicrobial metabolite 2-hexyl-5-propyl-resorcinol and introduction of the plasmid pPrn (Example 2) by conjugation.

*P. fluorescens* strain CGA319115 is a transposon mutant of the parent strain CGA267356 that is incapable of the production of 2-hexyl-5-propyl-resorcinol (subject of U.S. Pat. No. 5,496,547) and that provides greater biocontrol activity compared to strain CGA267356. A cosmid clone, BL3610, from a gene library of DNA from strain CGA267356 was found that restores production of 2-hexyl-5-propyl-resorcinol to strain CGA319115. An in vivo marker exchange was performed with cosmid clone BL3610 in strain CGA319115 in order to rescue the transposon and the flanking DNA. The cosmid clone BL3610Tn containing the mutagenized genomic DNA from strain CGA319115 with the transposon was thus isolated. A 6.5 kilobase pair (kb) EcoRI DNA fragment from cosmid BL3610 that corresponded to the region in cosmid BL3610Tn that contained the transposon insertion was cloned into plasmid pBluescript II (Pharmacea, Inc.) to create plasmid pBL3632.

The DNA sequence of this fragment and the DNA flanking the transposon in strain CGA319115 were determined and compared to reveal the precise location of the transposon insertion in the 6.5 kb DNA fragment. Two unique BclI restriction sites approximately 200 base pairs apart and flanking the transposon insertion site were identified within this region and the DNA between these sites was deleted by restriction with BclI and religation. A 4.0 kb XhoI DNA fragment derived from the 6.5 kb EcoRI fragment of pBL3632 and containing the deletion of the 200 base pair BclI fragment was cloned into a plasmid vector to facilitate homologous exchange in strain CGA267356. Homologous exchange between this plasmid and the chromosome of strain CGA267356 resulted in replacement of the wild-type region in the chromosome with the deleted DNA of the plasmid, thereby rendering the strain incapable of the production of 2-hexyl-5-propyl-resorcinol. Southern hybridization was performed to confirm that the BclI fragment was absent.

This 2-hexyl-5-propyl-resorcinol non-producing deletion mutant of *P. fluorescens* strain CGA267356 was given the strain name NOA402209. Strain NOA402212 was created in by introducing the deletion of the 200 bp BclI fragment into the chromosome of *P. fluorescens* strain CGA375260 (Example 1) as described above to create strain NOA402211 and by the subsequent introduction of the plasmid pPrn containing the prnABCD gene cluster under the control of the tac promoter.

Strain NOA402212 produces more pyrrolnitrin (Table 1) than parent strain CGA267356 and it provides greater biocontrol activity (Table 2) compared to the parent strain. Strain NOA402212 was deposited with the NRRL (Agricultural Research Service, Patent Culture Collection, Northern Regional Research Center, 1815 North University Street, Peoria, Ill. 61604, U.S.A) on Nov. 20, 1997, and assigned accession no. NRRLB-21892.

EXAMPLE 4
Construction of Strain NOA409063 (MONO686) (pGac*3/Prn)

Strain NOA409063 (a.k.a. MONO686) was constructed from the parent *P. fluorescens* strain CGA267356 by the introduction of a plasmid containing both the gac*3 and prnABCD genes.

Plasmid pGac*3/Prn was constructed by cloning the prnABCD gene cluster under the control of the tac promoter as a 6.9 kb BglII fragment (Example 2) into the unique BglII site of the broad host-range plasmid pVK101 (Knauf, V. and Nester, E. *Plasmid* 8:45-54 (1982)) followed by cloning the gac*3 gene (Example 1) as an XhoI DNA fragment into the unique XhoI site. This plasmid was introduced into the parent *P. fluorescens* strain CGA267356 to create strain NOA409063.

Strain NOA409063 produces more pyrrolnitrin (Table 1) and provides greater biocontrol activity (Table 2) than parent strain CGA267356. Strain NOA409063 was deposited with the 7 NRRL on Nov. 20, 1997, and assigned accession no. NRRL (Agricultural Research Service, Patent Culture Collection, Northern Regional Research Center, 1815 North University Street, Peoria, Ill. 61604, U.S.A) B-21902.

EXAMPLE 5
Construction of Strain NOA413175 (MONO707) (gac*3, pKT-Prn)

Strain NOA413175 (a.k.a. MONO707) was created by introduction of plasmid pKT-Prn by conjugation into the *P. fluorescens* strain CGA375260 (Example 1). Plasmid pKT-Prn was constructed by cloning the 6.9 kb BglII fragment described in Example 2 containing the prnABCD gene cluster from strain CGA267356 with the tac promoter and rrnB transcription terminator, into the broad host-range plasmid pKT231 (Pühler, Vectors for Gram-negative Bacteria. 1985. Elsevier Scientific Publishers). Strain NOA413175 produces more pyrrolnitrin (Table 1) and provides greater biocontrol activity (Table 2) than parent strain CGA267356. Strain NOA413175 was deposited with the NRRL (Agricultural Research Service, Patent Culture Collection, Northern Regional Research Center, 1815 North University Street, Peoria, Ill. 61604, U.S.A) on Nov. 20, 1997, and assigned accession no. NRRL B-21897.

EXAMPLE 6
Construction of Strain NOA413176 (MONO708) (gac*3, res, pKT-Prn)

Strain NOA413176 (a.k.a. MONO708) was created by introduction of plasmid pKT-Prn (Example 5) by conjugation into P. fluorescens strain NOA402211 (Example 3). Strain NOA413176 produces more pyrrolnitrin (Table 1) and provides greater biocontrol activity (Table 2) than parent strain CGA267356. Strain NOA413176 was deposited with the NRRL (Agricultural Research Service, Patent Culture Collection, Northern Regional Research Center, 1815 North University Street, Peoria, Ill. 61604, U.S.A) on Nov. 20, 1997, and assigned accession no. NRRL B-21898.

EXAMPLE 7
Cultivation of Bacteria and Fungi for Screening Assays

Cultivation of bacteria, cultivation of *Rhizoctonia solani*, and cultivation of *Pythium aphanidermatum* are done as described in Example 26 of U.S. patent application Ser. No. 08/977,306, incorporated herein by reference.

EXAMPLE 8
Assays For Biocontrol Activity

Preparation of bacterial cultures and fungal inocula, *Rhizoctonia solani*-cucumber assay, *Rhizoctonia solani*-impatiens assay, *Rhizoctonia solani*-poinsettia assay, and *Pythium aphanidermatum*-cucumber assay are as described in Example 27 of Ser. No. 08/977,306.

EXAMPLE 9
Extraction of Antifungal Metabolites

Active antifungal metabolites such as pyrrolnitrin (prn) can be extracted from the growth medium of bacterial strains as describe in Example 28 of Ser. No. 08/977,306.

EXAMPLE 10
Combination of Biocontrol Strain With Fungicides

The combined application of the biocontrol strains of the invention with a fungicide such as metalaxyl is as describe in Example 29 of Ser. No. 08/977,306.

EXAMPLE 11
Antifungal Compositions

Formulations of antifungal compositions containing as the active ingredient the antifungal metabolites that are produced by the biocontrol strains of the invention and that are inhibitory to the growth of fungi such as Rhizoctonia and Pythium are produced according to Examples 10 and 11 in U.S. Pat. No. 5,348,742.

EXAMPLE 12
Field Trials of Biocontrol Strains

Field trials of the biocontrol strains of the invention are done as described in Example 31 of Serial No. 08/977,306.

TABLE 1

Pyrrolnitrin production by *P. fluorescens* strain CGA267356 and genetically modified strains derived from it. Pyrrolnitrin was isolated from 3 day old cultures of the strains grown in CMMMAD medium by extraction with methanol and quantified by HPLC analysis.

| Strain | Pyrrolnitrin (mg/liter) |
|---|---|
| CGA267356 (MOCG134) | 40.0 |
| CGA375260 (MONO570) | 65.0 |
| NOA402208 (MONO630) | 250.0 |
| NOA402212 (MONO634) | 320.0 |
| NOA409063 (MONO686) | 245.0 |
| NOA413175 (MONO707) | 79.0 |
| NOA413176 (MONO708) | 55.0 |

TABLE 2

Biocontrol activity of *P. fluorescens* strain CGA267356 and genetically modified strains derived from it. The data presented is the control of Rhizoctonia on three plant types and Pythium on cucumbers only. All data is presented relative to the parent strain, CGA267356, applied at high (H) (= 100% biocontrol activity) and low (L) (= 0% biocontrol activity) rates equal to $2 \times 10^8$ and $2 \times 10^7$ cells/g soil, respectively.
All other strains were applied only at the low rate so that any relative biocontrol activity greater than 0 represents an improvement compared to the parent strain. All data are the mean of three experiments.
nd = not determined.

| | Relative Biocontrol Activity | | | |
|---|---|---|---|---|
| | Rhizoctonia | | | Pythium |
| Strain | Cucumber | Impatiens | Poinsettia | Cucumber |
| CGA267356 (H) | 100 | 100 | 100 | 100 |
| CGA267356 (L) | 0 | 0 | 0 | 0 |
| CGA375260 | 102 | 0 | 47 | 83 |
| NOA402208 | 225 | 130 | nd | 0 |
| NOA402212 | 125 | 80 | nd | 0 |
| NOA409063 | 400 | 117 | 102 | nd |
| NOA413175 | 125 | 17 | nd | nd |
| NOA413176 | 0 | 133 | nd | nd |

While the present invention has been described with reference to specific embodiments thereof, it will be appreciated that numerous variations, modifications, and embodiments are possible, and accordingly, all such variations, modifications and embodiments are to be regarded as being within the scope of the present invention.

What is claimed is:

1. An isolated DNA molecule that encodes a LemA-independent GacA regulatory protein, wherein:
   (a) said LemA-independent GacA regulatory protein has an isoleucine instead of a methionine residue in an amino acid position corresponding to position 20 of SEQ ID NO:2;
   (b) said LemA-independent GacA regulatory protein has an arginine instead of a glycine residue in an amino acid position corresponding to position 105 of SEQ ID NO:2;
   (c) said LemA-independent GacA regulatory protein has an arginine instead of a glutamine residue in an amino acid position corresponding to position 132 of SEQ ID NO:2; or
   (d) said LemA-independent GacA transcriptional activation element has a tyrosine instead of a cysteine residue in an amino acid position corresponding to position 84 of SEQ ID NO:2.

2. An isolated DNA molecule according to claim 1, wherein said DNA molecule is isolated from a Pseudomonas species.

3. An isolated DNA molecule according to claim 2, wherein said DNA molecule is isolated from *Pseudomonas fluorescens*.

4. An isolated DNA molecule according to claim 1, wherein said LemA-independent GacA regulatory protein has an isoleucine instead of a methionine residue in an amino acid position corresponding to position 20 of SEQ ID NO:2.

5. An isolated DNA molecule according to claim 1, wherein said LemA-independent GacA regulatory protein comprises the amino acid sequence shown in SEQ ID NO:4.

6. An isolated DNA molecule according to claim 5, wherein said DNA molecule comprises the nucleotide sequence shown in SEQ ID NO:3.

7. An isolated DNA molecule according to claim 1, wherein said LemA-independent GacA regulatory protein has an arginine instead of a glycine residue in an amino acid position corresponding to position 105 of SEQ ID NO:2.

8. An isolated DNA molecule according to claim 1, wherein said LemA-independent GacA regulatory protein comprises the amino acid sequence shown in SEQ ID NO:6.

9. An isolated DNA molecule according to claim 8, wherein said DNA molecule comprises the nucleotide sequence shown in SEQ ID NO:5.

10. An isolated DNA molecule according to claim 1, wherein said LemA-independent GacA regulatory protein has an arginine instead of a glutamine residue in an amino acid position corresponding to position 132 of SEQ ID NO:2.

11. An isolated DNA molecule according to claim 1, wherein said LemA-independent GacA regulatory protein comprises the amino acid sequence shown in SEQ ID NO:8.

12. An isolated DNA molecule according to claim 11 wherein said DNA molecule comprises the nucleotide sequence shown in SEQ ID NO:7.

13. An isolated DNA molecule according to claim 1, wherein said LemA-independent GacA regulatory protein has a tyrosine instead of a cysteine residue in an amino acid position corresponding to position 84 of SEQ ID NO:2.

14. An isolated DNA molecule according to claim 1, wherein said LemA-independent GacA regulatory protein comprises the amino acid sequence shown in SEQ ID NO:10.

15. An isolated DNA molecule according to claim 14, wherein said DNA molecule comprises the nucleotide sequence shown in SEQ ID NO:9.

16. A chimeric gene comprising a promoter operatively linked to the DNA molecule of claim 1.

17. A recombinant vector comprising the chimeric gene of claim 16 wherein said vector is capable of being stably transformed into a host cell.

18. A host cell stably transformed with the DNA molecule of claim 1, wherein said host cell is capable of expressing said DNA molecule.

19. A host cell of claim 18, which is a bacterial cell.

20. A host cell of claim 19, which is Pseudomonas.

21. A host cell of claim 20, which is *Pseudomonas fluorescens*.

22. An isolated LemA-independent GacA regulatory protein encoded by the DNA molecule of claim 1.

23. An isolated LemA-independent GacA regulatory protein according to claim 22 wherein said regulatory protein comprises the amino acid sequence set forth in SEQ ID NO:4, 6, 8, or 10.

24. A method of activating a gene that is latent or natively expressed at low levels in a bacterial strain, said method comprising introducing the DNA molecule of claim 1 into said bacterial strain.

25. A method according to claim 24, wherein said bacterial strain is Pseudomonas.

26. A method according to claim 25, wherein said bacterial strain is *Pseudomonas fluorescens*.

27. A method of rendering a Pseudomonas strain effective against fungal pathogens, said method comprising introducing into the Pseudomonas strain the DNA molecule of claim 1.

28. A method according to claim 3 wherein said Pseudomonas strain is *Pseudomonas fluorescens*.

\* \* \* \* \*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:

(A) LENGTH: 642 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pseudomonas fluorescens
(B) STRAIN: CGA267356 (aka MOCG134 and aka BL915)

(ix) FEATURE:
(A) NAME/KEY: CDS
(B) LOCATION: 1..639
(D) OTHER INFORMATION: /transl_except= (pos: 1 .. 3, aa: Met (xi) SEQUENCE DESCRIPTION: SEQ ID NO:1:

| | | | | | | | | | | | | | | | | |
|---|---|---|---|---|---|---|---|---|---|---|---|---|---|---|---|---|
| TTG | ATT | AGG | GTG | CTA | GTA | GTC | GAT | GAC | CAT | GAT | CTC | GTT | CGT | ACA | GGT | 48 |
| Met | Ile | Arg | Val | Leu | Val | Val | Asp | Asp | His | Asp | Leu | Val | Arg | Thr | Gly | |
| 1 | | | | 5 | | | | | 10 | | | | | 15 | | |
| ATT | ACA | CGA | ATG | CTG | GCT | GAC | ATC | GAT | GGC | CTG | CAA | GTG | GTC | GGC | CAG | 96 |
| Ile | Thr | Arg | Met | Leu | Ala | Asp | Ile | Asp | Gly | Leu | Gln | Val | Val | Gly | Gln | |
| | | | 20 | | | | | 25 | | | | | 30 | | | |
| GCC | GAG | TCA | GGG | GAG | GAA | TCC | CTG | CTC | AAG | GCC | CGG | GAG | TTG | AAA | CCC | 144 |
| Ala | Glu | Ser | Gly | Glu | Glu | Ser | Leu | Leu | Lys | Ala | Arg | Glu | Leu | Lys | Pro | |
| | | 35 | | | | | 40 | | | | | 45 | | | | |
| GAT | GTG | GTC | CTC | ATG | GAC | GTC | AAG | ATG | CCC | GGG | ATC | GGC | GGT | CTT | GAA | 192 |
| Asp | Val | Val | Leu | Met | Asp | Val | Lys | Met | Pro | Gly | Ile | Gly | Gly | Leu | Glu | |
| | 50 | | | | | 55 | | | | | 60 | | | | | |
| GCC | ACG | CGC | AAA | TTG | TTG | CGC | AGT | CAC | CCG | GAT | ATC | AAA | GTC | GTG | GCC | 240 |
| Ala | Thr | Arg | Lys | Leu | Leu | Arg | Ser | His | Pro | Asp | Ile | Lys | Val | Val | Ala | |
| 65 | | | | | 70 | | | | | 75 | | | | | 80 | |
| GTC | ACC | GTG | TGT | GAA | GAA | GAT | CCG | TTC | CCG | ACC | CGC | TTG | CTG | CAA | GCC | 288 |
| Val | Thr | Val | Cys | Glu | Glu | Asp | Pro | Phe | Pro | Thr | Arg | Leu | Leu | Gln | Ala | |
| | | | | 85 | | | | | 90 | | | | | 95 | | |
| GGC | GCG | GCG | GGT | TAC | CTG | ACC | AAG | GGG | GCG | GGC | CTC | AAT | GAA | ATG | GTG | 336 |
| Gly | Ala | Ala | Gly | Tyr | Leu | Thr | Lys | Gly | Ala | Gly | Leu | Asn | Glu | Met | Val | |
| | | | 100 | | | | | 105 | | | | | 110 | | | |
| CAG | GCC | ATT | CGC | CTG | GTG | TTT | GCC | GGC | CAG | CGT | TAC | ATC | AGC | CCG | CAA | 384 |
| Gln | Ala | Ile | Arg | Leu | Val | Phe | Ala | Gly | Gln | Arg | Tyr | Ile | Ser | Pro | Gln | |
| | | 115 | | | | | 120 | | | | | 125 | | | | |
| ATT | GCC | CAG | CAG | TTG | GTG | TTC | AAG | TCA | TTC | CAG | CCT | TCC | AGT | GAT | TCA | 432 |
| Ile | Ala | Gln | Gln | Leu | Val | Phe | Lys | Ser | Phe | Gln | Pro | Ser | Ser | Asp | Ser | |
| | | 130 | | | | | 135 | | | | | 140 | | | | |
| CCG | TTC | GAT | GCT | TTG | TCC | GAG | CGG | GAA | ATC | CAG | ATC | GCG | CTG | ATG | ATT | 480 |
| Pro | Phe | Asp | Ala | Leu | Ser | Glu | Arg | Glu | Ile | Gln | Ile | Ala | Leu | Met | Ile | |
| 145 | | | | | 150 | | | | | 155 | | | | | 160 | |
| GTC | GGC | TGC | CAG | AAA | GTG | CAG | ATC | ATC | TCC | GAC | AAG | CTG | TGC | CTG | TCT | 528 |
| Val | Gly | Cys | Gln | Lys | Val | Gln | Ile | Ile | Ser | Asp | Lys | Leu | Cys | Leu | Ser | |
| | | | | 165 | | | | | 170 | | | | | 175 | | |
| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser | |
| | | | 180 | | | | | 185 | | | | | 190 | | | |
| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met | |
| | | 195 | | | | | 200 | | | | | 205 | | | | |
| GTC | GAT | GCC | AGT | GCC | TGA | | | | | | | | | | | 642 |
| Val | Asp | Ala | Ser | Ala | | | | | | | | | | | | |
| | | 210 | | | | | | | | | | | | | | |

(2) INFORMATION FOR SEQ ID NO:2:

(i) SEQUENCE CHARACTERISTICS:
    (A) LENGTH: 213 amino acids
    (B) TYPE: amino acid
    (D) TOPOLOGY: linear (ii) MOLECULE TYPE: protein (xi) SEQUENCE DESCRIPTION: SEQ ID NO:2:

```
Met Ile Arg Val Leu Val Val Asp Asp His Asp Leu Val Arg Thr Gly
 1               5                  10                  15
Ile Thr Arg Met Leu Ala Asp Ile Asp Gly Leu Gln Val Val Gly Gln
            20                  25                  30
Ala Glu Ser Gly Glu Glu Ser Leu Leu Lys Ala Arg Glu Leu Lys Pro
            35                  40                  45
Asp Val Val Leu Met Asp Val Lys Met Pro Gly Ile Gly Gly Leu Glu
        50                  55                  60
Ala Thr Arg Lys Leu Leu Arg Ser His Pro Asp Ile Lys Val Val Ala
65                  70                  75                  80
Val Thr Val Cys Glu Glu Asp Pro Phe Pro Thr Arg Leu Leu Gln Ala
                85                  90                  95
Gly Ala Ala Gly Tyr Leu Thr Lys Gly Ala Gly Leu Asn Glu Met Val
                100                 105                 110
Gln Ala Ile Arg Leu Val Phe Ala Gly Gln Arg Tyr Ile Ser Pro Gln
            115                 120                 125
Ile Ala Gln Gln Leu Val Phe Lys Ser Phe Gln Pro Ser Ser Asp Ser
        130                 135                 140
Pro Phe Asp Ala Leu Ser Glu Arg Glu Ile Gln Ile Ala Leu Met Ile
145                 150                 155                 160
Val Gly Cys Gln Lys Val Gln Ile Ile Ser Asp Lys Leu Cys Leu Ser
                165                 170                 175
Pro Lys Thr Val Asn Thr Tyr Arg Tyr Arg Ile Phe Glu Lys Leu Ser
                180                 185                 190
Ile Ser Ser Asp Val Glu Leu Thr Leu Leu Ala Val Arg His Gly Met
            195                 200                 205
Val Asp Ala Ser Ala
210
```

(2) INFORMATION FOR SEQ ID NO:3:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: CGA375260

(ix) FEATURE:
        (A) NAME/KEY: CDS
        (B) LOCATION: 1..639
        (D) OTHER INFORMATION: /product="gac*1 gene"
        (D) OTHER INFORMATION: /transl_except= (pos: 1 .. 3, aa: Met (xi) SEQUENCE DESCRIPTION: SEQ ID NO:3:

```
TTG ATT AGG GTG CTA GTA GTC GAT GAC CAT GAT CTC GTT CGT ACA GGT    48
Met Ile Arg Val Leu Val Val Asp Asp His Asp Leu Val Arg Thr Gly
```

|  |  |  |  |  |  |  |  |  |  |  |  |  |  |  |  |  |
|---|---|---|---|---|---|---|---|---|---|---|---|---|---|---|---|---|
| 1 |  |  |  | 5 |  |  |  |  | 10 |  |  |  |  | 15 |  |  |
| ATT | ACA | CGA | ATA | CTG | GCT | GAC | ATC | GAT | GGC | CTG | CAA | GTG | GTC | GGC | CAG | 96 |
| Ile | Thr | Arg | Ile | Leu | Ala | Asp | Ile | Asp | Gly | Leu | Gln | Val | Val | Gly | Gln |  |
|  |  |  | 20 |  |  |  |  | 25 |  |  |  |  | 30 |  |  |  |
| GCC | GAG | TCA | GGG | GAG | GAA | TCC | CTG | CTC | AAG | GCC | CGG | GAG | TTG | AAA | CCC | 144 |
| Ala | Glu | Ser | Gly | Glu | Glu | Ser | Leu | Leu | Lys | Ala | Arg | Glu | Leu | Lys | Pro |  |
|  |  | 35 |  |  |  |  | 40 |  |  |  |  | 45 |  |  |  |  |
| GAT | GTG | GTC | CTC | ATG | GAC | GTC | AAG | ATG | CCC | GGG | ATC | GGC | GGT | CTT | GAA | 192 |
| Asp | Val | Val | Leu | Met | Asp | Val | Lys | Met | Pro | Gly | Ile | Gly | Gly | Leu | Glu |  |
|  | 50 |  |  |  |  | 55 |  |  |  |  | 60 |  |  |  |  |  |
| GCC | ACG | CGC | AAA | TTG | TTG | CGC | AGT | CAC | CCG | GAT | ATC | AAA | GTC | GTG | GCC | 240 |
| Ala | Thr | Arg | Lys | Leu | Leu | Arg | Ser | His | Pro | Asp | Ile | Lys | Val | Val | Ala |  |
| 65 |  |  |  |  | 70 |  |  |  |  | 75 |  |  |  |  | 80 |  |
| GTC | ACC | GTG | TGT | GAA | GAA | GAT | CCG | TTC | CCG | ACC | CGC | TTG | CTG | CAA | GCC | 288 |
| Val | Thr | Val | Cys | Glu | Glu | Asp | Pro | Phe | Pro | Thr | Arg | Leu | Leu | Gln | Ala |  |
|  |  |  |  | 85 |  |  |  |  | 90 |  |  |  |  | 95 |  |  |
| GGC | GCG | GCG | GGT | TAC | CTG | ACC | AAG | GGG | GCG | GGC | CTC | AAT | GAA | ATG | GTG | 336 |
| Gly | Ala | Ala | Gly | Tyr | Leu | Thr | Lys | Gly | Ala | Gly | Leu | Asn | Glu | Met | Val |  |
|  |  |  | 100 |  |  |  |  | 105 |  |  |  |  | 110 |  |  |  |
| CAG | GCC | ATT | CGC | CTG | GTG | TTT | GCC | GGC | CAG | CGT | TAC | ATC | AGC | CCG | CAA | 384 |
| Gln | Ala | Ile | Arg | Leu | Val | Phe | Ala | Gly | Gln | Arg | Tyr | Ile | Ser | Pro | Gln |  |
|  |  | 115 |  |  |  |  | 120 |  |  |  |  | 125 |  |  |  |  |
| ATT | GCC | CAG | CAG | TTG | GTG | TTC | AAG | TCA | TTC | CAG | CCT | TCC | AGT | GAT | TCA | 432 |
| Ile | Ala | Gln | Gln | Leu | Val | Phe | Lys | Ser | Phe | Gln | Pro | Ser | Ser | Asp | Ser |  |
|  | 130 |  |  |  |  | 135 |  |  |  |  | 140 |  |  |  |  |  |
| CCG | TTC | GAT | GCT | TTG | TCC | GAG | CGG | GAA | ATC | CAG | ATC | GCG | CTG | ATG | ATT | 480 |
| Pro | Phe | Asp | Ala | Leu | Ser | Glu | Arg | Glu | Ile | Gln | Ile | Ala | Leu | Met | Ile |  |
| 145 |  |  |  |  | 150 |  |  |  |  | 155 |  |  |  |  | 160 |  |
| GTC | GGC | TGC | CAG | AAA | GTG | CAG | ATC | ATC | TCC | GAC | AAG | CTG | TGC | CTG | TCT | 528 |
| Val | Gly | Cys | Gln | Lys | Val | Gln | Ile | Ile | Ser | Asp | Lys | Leu | Cys | Leu | Ser |  |
|  |  |  |  | 165 |  |  |  |  | 170 |  |  |  |  | 175 |  |  |
| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser |  |
|  |  |  | 180 |  |  |  |  | 185 |  |  |  |  | 190 |  |  |  |
| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met |  |
|  |  | 195 |  |  |  |  | 200 |  |  |  |  | 205 |  |  |  |  |
| GTC | GAT | GCC | AGT | GCC | TGA |  |  |  |  |  |  |  |  |  |  | 642 |
| Val | Asp | Ala | Ser | Ala |  |  |  |  |  |  |  |  |  |  |  |  |
| 210 |  |  |  |  |  |  |  |  |  |  |  |  |  |  |  |  |

( 2 ) INFORMATION FOR SEQ ID NO:4:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ile | Arg | Val | Leu | Val | Val | Asp | Asp | His | Asp | Leu | Val | Arg | Thr | Gly |
|---|---|---|---|---|---|---|---|---|---|---|---|---|---|---|---|
| 1 |  |  |  | 5 |  |  |  |  | 10 |  |  |  |  | 15 |  |
| Ile | Thr | Arg | Ile | Leu | Ala | Asp | Ile | Asp | Gly | Leu | Gln | Val | Val | Gly | Gln |
|  |  |  | 20 |  |  |  |  | 25 |  |  |  |  | 30 |  |  |
| Ala | Glu | Ser | Gly | Glu | Glu | Ser | Leu | Leu | Lys | Ala | Arg | Glu | Leu | Lys | Pro |
|  |  | 35 |  |  |  |  | 40 |  |  |  |  | 45 |  |  |  |
| Asp | Val | Val | Leu | Met | Asp | Val | Lys | Met | Pro | Gly | Ile | Gly | Gly | Leu | Glu |
|  | 50 |  |  |  |  | 55 |  |  |  |  | 60 |  |  |  |  |
| Ala | Thr | Arg | Lys | Leu | Leu | Arg | Ser | His | Pro | Asp | Ile | Lys | Val | Val | Ala |
| 65 |  |  |  |  | 70 |  |  |  |  | 75 |  |  |  |  | 80 |

| Val | Thr | Val | Cys | Glu | Glu | Asp | Pro | Phe | Pro | Thr | Arg | Leu | Leu | Gln | Ala |
|---|---|---|---|---|---|---|---|---|---|---|---|---|---|---|---|
| | | | | 85 | | | | | 90 | | | | | 95 | |

| Gly | Ala | Ala | Gly | Tyr | Leu | Thr | Lys | Gly | Ala | Gly | Leu | Asn | Glu | Met | Val |
|---|---|---|---|---|---|---|---|---|---|---|---|---|---|---|---|
| | | | 100 | | | | 105 | | | | | 110 | | | |

| Gln | Ala | Ile | Arg | Leu | Val | Phe | Ala | Gly | Gln | Arg | Tyr | Ile | Ser | Pro | Gln |
|---|---|---|---|---|---|---|---|---|---|---|---|---|---|---|---|
| | | | 115 | | | | 120 | | | | | 125 | | | |

| Ile | Ala | Gln | Gln | Leu | Val | Phe | Lys | Ser | Phe | Gln | Pro | Ser | Ser | Asp | Ser |
|---|---|---|---|---|---|---|---|---|---|---|---|---|---|---|---|
| | 130 | | | | | 135 | | | | | 140 | | | | |

| Pro | Phe | Asp | Ala | Leu | Ser | Glu | Arg | Glu | Ile | Gln | Ile | Ala | Leu | Met | Ile |
|---|---|---|---|---|---|---|---|---|---|---|---|---|---|---|---|
| 145 | | | | | 150 | | | | | 155 | | | | | 160 |

| Val | Gly | Cys | Gln | Lys | Val | Gln | Ile | Ile | Ser | Asp | Lys | Leu | Cys | Leu | Ser |
|---|---|---|---|---|---|---|---|---|---|---|---|---|---|---|---|
| | | | | 165 | | | | | 170 | | | | | 175 | |

| Pro | Lys | Thr | Val | Asn | Thr | Tyr | Arg | Tyr | Arg | Ile | Phe | Glu | Lys | Leu | Ser |
|---|---|---|---|---|---|---|---|---|---|---|---|---|---|---|---|
| | | | 180 | | | | | 185 | | | | | 190 | | |

| Ile | Ser | Ser | Asp | Val | Glu | Leu | Thr | Leu | Leu | Ala | Val | Arg | His | Gly | Met |
|---|---|---|---|---|---|---|---|---|---|---|---|---|---|---|---|
| | | 195 | | | | | 200 | | | | | 205 | | | |

| Val | Asp | Ala | Ser | Ala |
|---|---|---|---|---|
| | | 210 | | |

(2) INFORMATION FOR SEQ ID NO:5:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: CGA375260

(ix) FEATURE:
        (A) NAME/KEY: CDS
        (B) LOCATION: 1..639
        (D) OTHER INFORMATION: /product="gac*2 gene"
        (D) OTHER INFORMATION: /transl_except= (pos: 1 .. 3, aa: Met (xi) SEQUENCE DESCRIPTION: SEQ ID NO:5:

| TTG | ATT | AGG | GTG | CTA | GTA | GTC | GAT | GAC | CAT | GAT | CTC | GTT | CGT | ACA | GGT | 48 |
|---|---|---|---|---|---|---|---|---|---|---|---|---|---|---|---|---|
| Met | Ile | Arg | Val | Leu | Val | Val | Asp | Asp | His | Asp | Leu | Val | Arg | Thr | Gly | |
| 1 | | | | 5 | | | | | 10 | | | | | 15 | | |

| ATT | ACA | CGA | ATG | CTG | GCT | GAC | ATC | GAT | GGC | CTG | CAA | GTG | GTC | GGC | CAG | 96 |
|---|---|---|---|---|---|---|---|---|---|---|---|---|---|---|---|---|
| Ile | Thr | Arg | Met | Leu | Ala | Asp | Ile | Asp | Gly | Leu | Gln | Val | Val | Gly | Gln | |
| | | | 20 | | | | | 25 | | | | | 30 | | | |

| GCC | GAG | TCA | GGG | GAG | GAA | TCC | CTG | CTC | AAG | GCC | CGG | GAG | TTG | AAA | CCC | 144 |
|---|---|---|---|---|---|---|---|---|---|---|---|---|---|---|---|---|
| Ala | Glu | Ser | Gly | Glu | Glu | Ser | Leu | Leu | Lys | Ala | Arg | Glu | Leu | Lys | Pro | |
| | | 35 | | | | | 40 | | | | | 45 | | | | |

| GAT | GTG | GTC | CTC | ATG | GAC | GTC | AAG | ATG | CCC | GGG | ATC | GGC | GGT | CTT | GAA | 192 |
|---|---|---|---|---|---|---|---|---|---|---|---|---|---|---|---|---|
| Asp | Val | Val | Leu | Met | Asp | Val | Lys | Met | Pro | Gly | Ile | Gly | Gly | Leu | Glu | |
| | 50 | | | | | 55 | | | | | 60 | | | | | |

| GCC | ACG | CGC | AAA | TTG | TTG | CGC | AGT | CAC | CCG | GAT | ATC | AAA | GTC | GTG | GCC | 240 |
|---|---|---|---|---|---|---|---|---|---|---|---|---|---|---|---|---|
| Ala | Thr | Arg | Lys | Leu | Leu | Arg | Ser | His | Pro | Asp | Ile | Lys | Val | Val | Ala | |
| 65 | | | | | 70 | | | | | 75 | | | | | 80 | |

| GTC | ACC | GTG | TGT | GAA | GAA | GAT | CCG | TTC | CCG | ACC | CGC | TTG | CTG | CAA | GCC | 288 |
|---|---|---|---|---|---|---|---|---|---|---|---|---|---|---|---|---|
| Val | Thr | Val | Cys | Glu | Glu | Asp | Pro | Phe | Pro | Thr | Arg | Leu | Leu | Gln | Ala | |
| | | | | 85 | | | | | 90 | | | | | 95 | | |

| GGC | GCG | GCG | GGT | TAC | CTG | ACC | AAG | AGG | GCG | GGC | CTC | AAT | GAA | ATG | GTG | 336 |
|---|---|---|---|---|---|---|---|---|---|---|---|---|---|---|---|---|
| Gly | Ala | Ala | Gly | Tyr | Leu | Thr | Lys | Arg | Ala | Gly | Leu | Asn | Glu | Met | Val | |

```
                              100                         105                         110
CAG  GCC  ATT  CGC  CTG  GTG  TTT  GCC  GGC  CAG  CGT  TAC  ATC  AGC  CCG  CAA           384
Gln  Ala  Ile  Arg  Leu  Val  Phe  Ala  Gly  Gln  Arg  Tyr  Ile  Ser  Pro  Gln
          115                      120                      125

ATT  GCC  CAG  CAG  TTG  GTG  TTC  AAG  TCA  TTC  CAG  CCT  TCC  AGT  GAT  TCA           432
Ile  Ala  Gln  Gln  Leu  Val  Phe  Lys  Ser  Phe  Gln  Pro  Ser  Ser  Asp  Ser
     130                      135                      140

CCG  TTC  GAT  GCT  TTG  TCC  GAG  CGG  GAA  ATC  CAG  ATC  GCG  CTG  ATG  ATT           480
Pro  Phe  Asp  Ala  Leu  Ser  Glu  Arg  Glu  Ile  Gln  Ile  Ala  Leu  Met  Ile
145                           150                      155                      160

GTC  GGC  TGC  CAG  AAA  GTG  CAG  ATC  ATC  TCC  GAC  AAG  CTG  TGC  CTG  TCT           528
Val  Gly  Cys  Gln  Lys  Val  Gln  Ile  Ile  Ser  Asp  Lys  Leu  Cys  Leu  Ser
                ようこそ 165                    170                      175

CCG  AAA  ACC  GTT  AAT  ACC  TAC  CGT  TAC  CGC  ATC  TTC  GAA  AAG  CTC  TCG           576
Pro  Lys  Thr  Val  Asn  Thr  Tyr  Arg  Tyr  Arg  Ile  Phe  Glu  Lys  Leu  Ser
               180                      185                      190

ATC  AGC  AGC  GAT  GTT  GAA  CTG  ACA  TTG  CTG  GCG  GTT  CGC  CAC  GGC  ATG           624
Ile  Ser  Ser  Asp  Val  Glu  Leu  Thr  Leu  Leu  Ala  Val  Arg  His  Gly  Met
          195                      200                      205

GTC  GAT  GCC  AGT  GCC  TGA                                                             642
Val  Asp  Ala  Ser  Ala
210
```

( 2 ) INFORMATION FOR SEQ ID NO:6:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ile  Arg  Val  Leu  Val  Val  Asp  Asp  His  Asp  Leu  Val  Arg  Thr  Gly
 1                  5                        10                       15

Ile  Thr  Arg  Met  Leu  Ala  Asp  Ile  Asp  Gly  Leu  Gln  Val  Val  Gly  Gln
               20                       25                       30

Ala  Glu  Ser  Gly  Glu  Glu  Ser  Leu  Leu  Lys  Ala  Arg  Glu  Leu  Lys  Pro
          35                       40                       45

Asp  Val  Val  Leu  Met  Asp  Val  Lys  Met  Pro  Gly  Ile  Gly  Gly  Leu  Glu
     50                       55                       60

Ala  Thr  Arg  Lys  Leu  Leu  Arg  Ser  His  Pro  Asp  Ile  Lys  Val  Val  Ala
65                       70                       75                       80

Val  Thr  Val  Cys  Glu  Glu  Asp  Pro  Phe  Pro  Thr  Arg  Leu  Leu  Gln  Ala
                    85                       90                       95

Gly  Ala  Ala  Gly  Tyr  Leu  Thr  Lys  Arg  Ala  Gly  Leu  Asn  Glu  Met  Val
               100                      105                      110

Gln  Ala  Ile  Arg  Leu  Val  Phe  Ala  Gly  Gln  Arg  Tyr  Ile  Ser  Pro  Gln
          115                      120                      125

Ile  Ala  Gln  Gln  Leu  Val  Phe  Lys  Ser  Phe  Gln  Pro  Ser  Ser  Asp  Ser
     130                      135                      140

Pro  Phe  Asp  Ala  Leu  Ser  Glu  Arg  Glu  Ile  Gln  Ile  Ala  Leu  Met  Ile
145                      150                      155                      160

Val  Gly  Cys  Gln  Lys  Val  Gln  Ile  Ile  Ser  Asp  Lys  Leu  Cys  Leu  Ser
                    165                      170                      175

Pro  Lys  Thr  Val  Asn  Thr  Tyr  Arg  Tyr  Arg  Ile  Phe  Glu  Lys  Leu  Ser
               180                      185                      190

Ile  Ser  Ser  Asp  Val  Glu  Leu  Thr  Leu  Leu  Ala  Val  Arg  His  Gly  Met
          195                      200                      205
```

```
Val  Asp  Ala  Ser  Ala
     210
```

( 2 ) INFORMATION FOR SEQ ID NO:7:

( i ) SEQUENCE CHARACTERISTICS:
        ( A ) LENGTH: 642 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: CGA375260

( i x ) FEATURE:
        ( A ) NAME/KEY: CDS
        ( B ) LOCATION: 1..639
        ( D ) OTHER INFORMATION: /product="gac*3 gene"
        ( D ) OTHER INFORMATION: /transl_except= (pos: 1 .. 3, aa: Met ( x i ) SEQUENCE DESCRIPTION: SEQ ID NO:7:

```
TTG  ATT  AGG  GTG  CTA  GTA  GTC  GAT  GAC  CAT  GAT  CTC  GTT  CGT  ACA  GGT        48
Met  Ile  Arg  Val  Leu  Val  Val  Asp  Asp  His  Asp  Leu  Val  Arg  Thr  Gly
 1                  5                        10                       15

ATT  ACA  CGA  ATG  CTG  GCT  GAC  ATC  GAT  GGC  CTG  CAA  GTG  GTC  GGC  CAG        96
Ile  Thr  Arg  Met  Leu  Ala  Asp  Ile  Asp  Gly  Leu  Gln  Val  Val  Gly  Gln
              20                       25                       30

GCC  GAG  TCA  GGG  GAG  GAA  TCC  CTG  CTC  AAG  GCC  CGG  GAG  TTG  AAA  CCC       144
Ala  Glu  Ser  Gly  Glu  Glu  Ser  Leu  Leu  Lys  Ala  Arg  Glu  Leu  Lys  Pro
          35                       40                       45

GAT  GTG  GTC  CTC  ATG  GAC  GTC  AAG  ATG  CCC  GGG  ATC  GGC  GGT  CTT  GAA       192
Asp  Val  Val  Leu  Met  Asp  Val  Lys  Met  Pro  Gly  Ile  Gly  Gly  Leu  Glu
     50                       55                       60

GCC  ACG  CGC  AAA  TTG  TTG  CGC  AGT  CAC  CCG  GAT  ATC  AAA  GTC  GTG  GCC       240
Ala  Thr  Arg  Lys  Leu  Leu  Arg  Ser  His  Pro  Asp  Ile  Lys  Val  Val  Ala
 65                  70                       75                       80

GTC  ACC  GTG  TGT  GAA  GAA  GAT  CCG  TTC  CCG  ACC  CGC  TTG  CTG  CAA  GCC       288
Val  Thr  Val  Cys  Glu  Glu  Asp  Pro  Phe  Pro  Thr  Arg  Leu  Leu  Gln  Ala
                    85                       90                       95

GGC  GCG  GCG  GGT  TAC  CTG  ACC  AAG  GGG  GCG  GGC  CTC  AAT  GAA  ATG  GTG       336
Gly  Ala  Ala  Gly  Tyr  Leu  Thr  Lys  Gly  Ala  Gly  Leu  Asn  Glu  Met  Val
               100                      105                      110

CAG  GCC  ATT  CGC  CTG  GTG  TTT  GCC  GGC  CAG  CGT  TAC  ATC  AGC  CCG  CAA       384
Gln  Ala  Ile  Arg  Leu  Val  Phe  Ala  Gly  Gln  Arg  Tyr  Ile  Ser  Pro  Gln
          115                      120                      125

ATT  GCC  CAG  CGG  TTG  GTG  TTC  AAG  TCA  TTC  CAG  CCT  TCC  AGT  GAT  TCA       432
Ile  Ala  Gln  Arg  Leu  Val  Phe  Lys  Ser  Phe  Gln  Pro  Ser  Ser  Asp  Ser
     130                      135                      140

CCG  TTC  GAT  GCT  TTG  TCC  GAG  CGG  GAA  ATC  CAG  ATC  GCG  CTG  ATG  ATT       480
Pro  Phe  Asp  Ala  Leu  Ser  Glu  Arg  Glu  Ile  Gln  Ile  Ala  Leu  Met  Ile
145                      150                      155                      160

GTC  GGC  TGC  CAG  AAA  GTG  CAG  ATC  ATC  TCC  GAC  AAG  CTG  TGC  CTG  TCT       528
Val  Gly  Cys  Gln  Lys  Val  Gln  Ile  Ile  Ser  Asp  Lys  Leu  Cys  Leu  Ser
                    165                      170                      175

CCG  AAA  ACC  GTT  AAT  ACC  TAC  CGT  TAC  CGC  ATC  TTC  GAA  AAG  CTC  TCG       576
Pro  Lys  Thr  Val  Asn  Thr  Tyr  Arg  Tyr  Arg  Ile  Phe  Glu  Lys  Leu  Ser
               180                      185                      190

ATC  AGC  AGC  GAT  GTT  GAA  CTG  ACA  TTG  CTG  GCG  GTT  CGC  CAC  GGC  ATG       624
Ile  Ser  Ser  Asp  Val  Glu  Leu  Thr  Leu  Leu  Ala  Val  Arg  His  Gly  Met
```

```
                            195                 200                 205
GTC GAT GCC AGT GCC TGA                                                                              642
Val Asp Ala Ser Ala
    210
```

( 2 ) INFORMATION FOR SEQ ID NO:8:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ile Arg Val Leu Val Val Asp Asp His Asp Leu Val Arg Thr Gly
  1               5                  10                  15
Ile Thr Arg Met Leu Ala Asp Ile Asp Gly Leu Gln Val Val Gly Gln
             20                  25                  30
Ala Glu Ser Gly Glu Glu Ser Leu Leu Lys Ala Arg Glu Leu Lys Pro
         35                  40                  45
Asp Val Leu Met Asp Val Lys Met Pro Gly Ile Gly Gly Leu Glu
     50                  55                  60
Ala Thr Arg Lys Leu Leu Arg Ser His Pro Asp Ile Lys Val Val Ala
 65                  70                  75                  80
Val Thr Val Cys Glu Glu Asp Pro Phe Pro Thr Arg Leu Leu Gln Ala
                 85                  90                  95
Gly Ala Ala Gly Tyr Leu Thr Lys Gly Ala Gly Leu Asn Glu Met Val
                100                 105                 110
Gln Ala Ile Arg Leu Val Phe Ala Gly Gln Arg Tyr Ile Ser Pro Gln
            115                 120                 125
Ile Ala Gln Arg Leu Val Phe Lys Ser Phe Gln Pro Ser Ser Asp Ser
130                 135                 140
Pro Phe Asp Ala Leu Ser Glu Arg Glu Ile Gln Ile Ala Leu Met Ile
145                 150                 155                 160
Val Gly Cys Gln Lys Val Gln Ile Ile Ser Asp Lys Leu Cys Leu Ser
                165                 170                 175
Pro Lys Thr Val Asn Thr Tyr Arg Tyr Arg Ile Phe Glu Lys Leu Ser
                180                 185                 190
Ile Ser Ser Asp Val Glu Leu Thr Leu Leu Ala Val Arg His Gly Met
            195                 200                 205
Val Asp Ala Ser Ala
    210
```

( 2 ) INFORMATION FOR SEQ ID NO:9:

( i ) SEQUENCE CHARACTERISTICS:
        ( A ) LENGTH: 642 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: CGA375260

( i x ) FEATURE:
        ( A ) NAME/KEY: CDS (B) LOCATION: 1..639
(D) OTHER INFORMATION: /product="gac*4 gene"
(D) OTHER INFORMATION: /transl_except= (pos: 1 .. 3, aa: Met (xi) SEQUENCE DESCRIPTION: SEQ ID NO:9:

| TTG | ATT | AGG | GTG | CTA | GTA | GTC | GAT | GAC | CAT | GAT | CTC | GTT | CGT | ACA | GGT | 48 |
| Met | Ile | Arg | Val | Leu | Val | Val | Asp | Asp | His | Asp | Leu | Val | Arg | Thr | Gly | |
| 1 | | | | 5 | | | | | 10 | | | | | 15 | | |

| ATT | ACA | CGA | ATG | CTG | GCT | GAC | ATC | GAT | GGC | CTG | CAA | GTG | GTC | GGC | CAG | 96 |
| Ile | Thr | Arg | Met | Leu | Ala | Asp | Ile | Asp | Gly | Leu | Gln | Val | Val | Gly | Gln | |
| | | | 20 | | | | | 25 | | | | | 30 | | | |

| GCC | GAG | TCA | GGG | GAG | GAA | TCC | CTG | CTC | AAG | GCC | CGG | GAG | TTG | AAA | CCC | 144 |
| Ala | Glu | Ser | Gly | Glu | Glu | Ser | Leu | Leu | Lys | Ala | Arg | Glu | Leu | Lys | Pro | |
| | | 35 | | | | | 40 | | | | | 45 | | | | |

| GAT | GTG | GTC | CTC | ATG | GAC | GTC | AAG | ATG | CCC | GGG | ATC | GGC | GGT | CTT | GAA | 192 |
| Asp | Val | Val | Leu | Met | Asp | Val | Lys | Met | Pro | Gly | Ile | Gly | Gly | Leu | Glu | |
| | 50 | | | | | 55 | | | | | 60 | | | | | |

| GCC | ACG | CGC | AAA | TTG | TTG | CGC | AGT | CAC | CCG | GAT | ATC | AAA | GTC | GTG | GCC | 240 |
| Ala | Thr | Arg | Lys | Leu | Leu | Arg | Ser | His | Pro | Asp | Ile | Lys | Val | Val | Ala | |
| 65 | | | | | 70 | | | | | 75 | | | | | 80 | |

| GTC | ACC | GTG | TAT | GAA | GAA | GAT | CCG | TTC | CCG | ACC | CGC | TTG | CTG | CAA | GCC | 288 |
| Val | Thr | Val | Tyr | Glu | Glu | Asp | Pro | Phe | Pro | Thr | Arg | Leu | Leu | Gln | Ala | |
| | | | | 85 | | | | | 90 | | | | | 95 | | |

| GGC | GCG | GCG | GGT | TAC | CTG | ACC | AAG | GGG | GCG | GGC | CTC | AAT | GAA | ATG | GTG | 336 |
| Gly | Ala | Ala | Gly | Tyr | Leu | Thr | Lys | Gly | Ala | Gly | Leu | Asn | Glu | Met | Val | |
| | | | 100 | | | | | 105 | | | | | 110 | | | |

| CAG | GCC | ATT | CGC | CTG | GTG | TTT | GCC | GGC | CAG | CGT | TAC | ATC | AGC | CCG | CAA | 384 |
| Gln | Ala | Ile | Arg | Leu | Val | Phe | Ala | Gly | Gln | Arg | Tyr | Ile | Ser | Pro | Gln | |
| | | 115 | | | | | 120 | | | | | 125 | | | | |

| ATT | GCC | CAG | CAG | TTG | GTG | TTC | AAG | TCA | TTC | CAG | CCT | TCC | AGT | GAT | TCA | 432 |
| Ile | Ala | Gln | Gln | Leu | Val | Phe | Lys | Ser | Phe | Gln | Pro | Ser | Ser | Asp | Ser | |
| | 130 | | | | | 135 | | | | | 140 | | | | | |

| CCG | TTC | GAT | GCT | TTG | TCC | GAG | CGG | GAA | ATC | CAG | ATC | GCG | CTG | ATG | ATT | 480 |
| Pro | Phe | Asp | Ala | Leu | Ser | Glu | Arg | Glu | Ile | Gln | Ile | Ala | Leu | Met | Ile | |
| 145 | | | | | 150 | | | | | 155 | | | | | 160 | |

| GTC | GGC | TGC | CAG | AAA | GTG | CAG | ATC | ATC | TCC | GAC | AAG | CTG | TGC | CTG | TCT | 528 |
| Val | Gly | Cys | Gln | Lys | Val | Gln | Ile | Ile | Ser | Asp | Lys | Leu | Cys | Leu | Ser | |
| | | | | 165 | | | | | 170 | | | | | 175 | | |

| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser | |
| | | | 180 | | | | | 185 | | | | | 190 | | | |

| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met | |
| | 195 | | | | | 200 | | | | | 205 | | | | | |

| GTC | GAT | GCC | AGT | GCC | TGA | | | | | | | | | | | 642 |
| Val | Asp | Ala | Ser | Ala | | | | | | | | | | | | |
| 210 | | | | | | | | | | | | | | | | |

(2) INFORMATION FOR SEQ ID NO:10:

(i) SEQUENCE CHARACTERISTICS:
(A) LENGTH: 213 amino acids
(B) TYPE: amino acid
(D) TOPOLOGY: linear (ii) MOLECULE TYPE: protein (xi) SEQUENCE DESCRIPTION: SEQ ID NO:10:

| Met | Ile | Arg | Val | Leu | Val | Val | Asp | Asp | His | Asp | Leu | Val | Arg | Thr | Gly |
| 1 | | | | 5 | | | | | 10 | | | | | 15 | |

| Ile | Thr | Arg | Met | Leu | Ala | Asp | Ile | Asp | Gly | Leu | Gln | Val | Val | Gly | Gln |
| | | | 20 | | | | | 25 | | | | | 30 | | |

-continued

| Ala | Glu | Ser | Gly | Glu | Glu | Ser | Leu | Leu | Lys | Ala | Arg | Glu | Leu | Lys | Pro |
|---|---|---|---|---|---|---|---|---|---|---|---|---|---|---|---|
| | | 35 | | | | | 40 | | | | | 45 | | | |
| Asp | Val | Val | Leu | Met | Asp | Val | Lys | Met | Pro | Gly | Ile | Gly | Gly | Leu | Glu |
| | 50 | | | | | 55 | | | | | 60 | | | | |
| Ala | Thr | Arg | Lys | Leu | Leu | Arg | Ser | His | Pro | Asp | Ile | Lys | Val | Val | Ala |
| 65 | | | | | 70 | | | | | 75 | | | | | 80 |
| Val | Thr | Val | Tyr | Glu | Glu | Asp | Pro | Phe | Pro | Thr | Arg | Leu | Leu | Gln | Ala |
| | | | | 85 | | | | | 90 | | | | | 95 | |
| Gly | Ala | Ala | Gly | Tyr | Leu | Thr | Lys | Gly | Ala | Gly | Leu | Asn | Glu | Met | Val |
| | | | 100 | | | | | 105 | | | | | 110 | | |
| Gln | Ala | Ile | Arg | Leu | Val | Phe | Ala | Gly | Gln | Arg | Tyr | Ile | Ser | Pro | Gln |
| | | 115 | | | | | 120 | | | | | 125 | | | |
| Ile | Ala | Gln | Gln | Leu | Val | Phe | Lys | Ser | Phe | Gln | Pro | Ser | Ser | Asp | Ser |
| | 130 | | | | | 135 | | | | | 140 | | | | |
| Pro | Phe | Asp | Ala | Leu | Ser | Glu | Arg | Glu | Ile | Gln | Ile | Ala | Leu | Met | Ile |
| 145 | | | | | 150 | | | | | 155 | | | | | 160 |
| Val | Gly | Cys | Gln | Lys | Val | Gln | Ile | Ile | Ser | Asp | Lys | Leu | Cys | Leu | Ser |
| | | | | 165 | | | | | 170 | | | | | 175 | |
| Pro | Lys | Thr | Val | Asn | Thr | Tyr | Arg | Tyr | Arg | Ile | Phe | Glu | Lys | Leu | Ser |
| | | | 180 | | | | | 185 | | | | | 190 | | |
| Ile | Ser | Ser | Asp | Val | Glu | Leu | Thr | Leu | Leu | Ala | Val | Arg | His | Gly | Met |
| | | 195 | | | | | 200 | | | | | 205 | | | |
| Val | Asp | Ala | Ser | Ala | | | | | | | | | | | |
| | 210 | | | | | | | | | | | | | | |